United States Patent

Lochead et al.

[11] Patent Number: 6,057,321
[45] Date of Patent: May 2, 2000

[54] 1,4-DIAZABICYCLO [2.2.2] OCT-2-YLMETHYL DERIVATIVES, THEIR PREPARATION AND THERAPEUTIC APPLICATION

[75] Inventors: Alistair Lochead, Charenton; Samir Jegham, Argenteuil; Alain Nedelec, Colombes; Axelle Solignac, Paris, all of France

[73] Assignee: Sanofi-Synthelabo, Paris, France

[21] Appl. No.: 09/319,413

[22] PCT Filed: Dec. 2, 1997

[86] PCT No.: PCT/FR97/02174

§ 371 Date: Jun. 4, 1999

§ 102(e) Date: Jun. 4, 1999

[87] PCT Pub. No.: WO98/24790

PCT Pub. Date: Jun. 11, 1998

[30] Foreign Application Priority Data

Dec. 4, 1996 [FR] France .................................. 96 14847

[51] Int. Cl.[7] ...................... A61K 31/529; C07D 487/08
[52] U.S. Cl. .......................... 514/249; 544/351; 544/352
[58] Field of Search .......................... 514/249; 544/351, 544/352

[56] References Cited

U.S. PATENT DOCUMENTS 4,772,459  9/1988  Sun et al. ................................. 424/10
5,663,173  9/1997  Jegham et al. ........................... 514/249

Primary Examiner—Michael G. Ambrose
Attorney, Agent, or Firm—Foley & Lardner

[57] ABSTRACT

The invention concerns compounds of general formula (I)

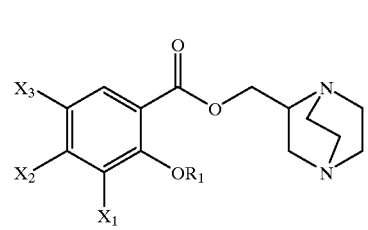

in which $R_1$ represents a methyl group, $X_1$ represents a hydrogen atom, or $OR_1$ and $X_1$ together form a group of formula $-O(CH_2)_2-, -O(CH_2)_3-, -O(CH_2)_2O-$ or $-O(CH_2)_3O-$, $X_2$ represents a hydrogen atom or an amino group, and $X_3$ representing a halogen atom. The compounds are ligands of serotoninergic receptors of the 5-$HT_3$ and/or 5-$HT_4$ types, and act as 5-$HT_4$ agonists and/or 5-$HT_3$ antogonists.

17 Claims, No Drawings

1,4-DIAZABICYCLO [2.2.2] OCT-2-YLMETHYL DERIVATIVES, THEIR PREPARATION AND THERAPEUTIC APPLICATION

The subject-matter of the present invention is 1,4-diazabicyclo[2.2.2]oct-2-ylmethyl benzoate derivatives, their preparation and their application in therapeutics.

The compounds of the invention correspond to the general formula (I)

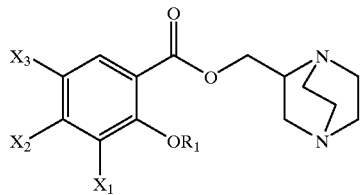

(I)

in which $R_1$ represents a methyl croup, $X_1$ represents a hydrogen atom, or $OR_1$ and $X_1$ together form a group of formula $-O(CH_2)_2-$, $-O(CH_2)_3-$, $-O(CH_2)_2O-$ or $-O(CH_2)_3O-$, $X_2$ represents a hydrogen atom or an amino group, and $X_3$ represents a halogen atom.

They can exist in the form of free bases or of addition salts with acids. Furthermore, they comprise an asymmetric carbon atom in the diazabicyclooctane ring and can therefore exist in the form of pure enantiomers or of mixtures of enantiomers.

According to the invention, the compounds of general formula (I) are prepared by a process illustrated by the following scheme.

Scheme

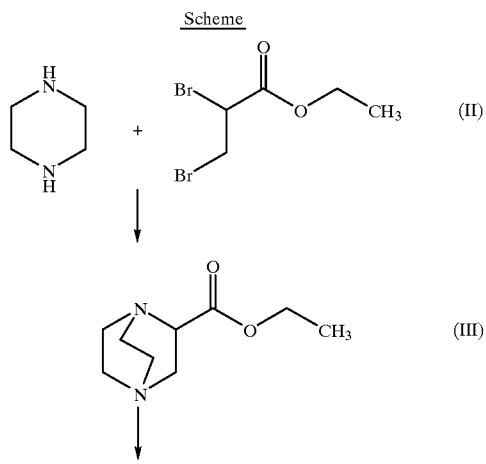

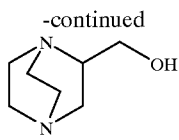

(IV)

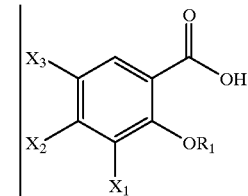

(V)

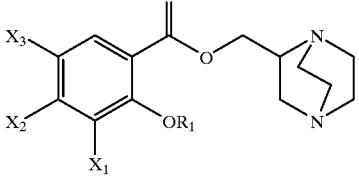

(I)

Ethyl 1,4-diazabicyclo[2.2.2]octane-2-carboxylate of formula (III) (described in *Helv. Chimica Acta* (1962), Vol. XLV, Part VII, No. 273 2383) is first prepared by reaction between piperazine and ethyl 2,3-dibromopropanoate in an inert solvent, for example toluene or benzene, and optionally in the presence of an organic base, for example triethylamine, then the ester obtained is reduced to 1,4-diazabicyclo[2.2.2]octane-2-methanol of formula (IV) (described in *Khim. Farm.* Zh. (1989), 23, 30–35 and in *Khim. Geterosikl. Soedin.* (1980), 10, 1404–1407), for example by means of lithium aluminium hydride, and, finally, the alcohol obtained is treated with a benzoic acid derivative of general formula (V), in which $R_1$, $X_1$, $X_2$ and X3 are as defined above, according to any known esterification method, for example by activation of the acid by means of an imidazolide and by coupling of the latter with the alcohol, converted beforehand to alkoxide, for example by means of butyllithium.

Piperazine and ethyl 2,3-dibromopropanoate are commercially available. Some benzoic acid derivatives of general formula (V) are commercially available; the others can be prepared by methods such as those disclosed in *J. Med. Chem.* (1993), 36, 4121–4123 and in Patent Applications EP-0234872, WO-9305038 and ES-2019042 or by saponification of corresponding esters, such as those disclosed in Patents DE-3001328 and DE-36433103.

The following example illustrates in detail the preparation of a compound according to the invention. The elemental microanalyses and the IR and NMR spectra confirm the structures of the compounds obtained.

EXAMPLE (1,4-Diazabicyclo[2.2.2]oct-2-yl)methyl 8-amino-7-chloro-2,3-dihydro-1,4-benzodioxine-5-carboxylate.

1. Ethyl 1,4-diazabicyclo[2.2.2]octane-2-carboxylate.

16.9 ml (116 mmol) of ethyl 2,3-dibromopropanoate, in solution in 250 ml of toluene, 10. g (116 mmol) of piperazine and 49.ml (348 mmol) of triethylamine, in solution in 150 ml of toluene, are successively introduced into a round-bottomed flask and the mixture is heated at 80° C. with magnetic stirring overnight. The mixture is cooled, the triethylamine hydrobromide is separated off by filtration, they being rinsed with ethyl acetate, the solvents are evaporated from the filtrate under reduced pressure and the residue is distilled at ambient pressure. 6.91 g of compound are obtained, which compound is used as is in the following stage.

2. 1,4-Diazabicyclo[2.2.2]octane-2-methanol.

0.21 g (5.43 mmol) of lithium aluminium hydride, in suspension in diethyl ether, is introduced into a round-bottomed flask, the suspension is cooled to 0° C. using an ice-cold bath, 1 g (5.43 mmol) of ethyl 1,4-diazabicyclo [2.2.2]octane-2-carboxy-ate, in solution in 10 ml of diethyl ether, is slowly added with magnetic stirring and the mixture is stirred at room temperature for 1 h.

The excess hydride is hydrolysed by slow addition of 0.2 ml of water, 0.2 ml of 15% aqueous sodium hydroxide solution and then a further 0.6 ml of water, the solid is separated off by filtration, it being rinsed with chloroform, and the filtrate is evaporated under reduced pressure.

After distillation, 0.43 g of oily product is obtained.

3. (1,4-Diazabicyclo[2.2.2]oct-2-yl)methyl 8-amino-7-chloro-2,3-dihydro-1,4-benzodioxine-5-carboxylate.

0.69 g (3.03 mmol) of 8-amino-7-chloro-2,3-dihydro-1, 4-benzodioxine-5-carboxylic acid, in suspension in 5 ml of anhydrous tetrahydrofuran, is introduced into a round-bottomed flask, 0.49 g (3.03 mmol) of N,N'-carbonyldiimidazole is added, under a nitrogen atmosphere and at room temperature, and the mixture is stirred for 2 h. 0.43 g (3.02 mmol) of 1,4-diazabicyclo[2.2.2]octane-2-methanol, in solution in 20 ml of tetrahydrofuran, is introduced into another round-bottomed flask and 1.21 ml (3.02 mmol) of a 2.5M solution of butyllithium in hexane are slowly added, under an argon atmosphere and with magnetic stirring, and the stirring is continued for 1 h.

The acid solution prepared above is then slowly added, using a syringe, to the butyllithium solution and stirring is continued for 1 h 10 min at room temperature.

The solvent is evaporated under reduced pressure, the residue is taken up in ethyl acetate and water, and the organic phase is separated off and washed several times with water. After drying, evaporating, taking up the residue in diethyl ether and recrystallizing from ethanol, 0.35 g of white solid is isolated. Melting point: 217° C.

The chemical structures and the physical properties of some compounds of the invention are illustrated in the following table.

TABLE

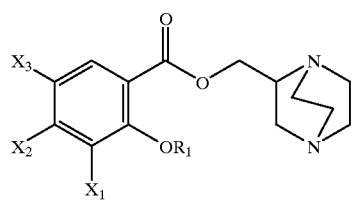

(I)

| No. | OR$_1$ | X$_1$ | X$_2$ | X$_3$ | Salt | M.p. (° C.) |
|---|---|---|---|---|---|---|
| 1 | —OCH$_3$ | H | H | Cl | — | 121–124 |
| 2 | —OCH$_3$ | H | —NH$_2$ | Cl | — | 168–171 |
| 3 | —O(CH$_2$)$_2$— | H | Cl | HCl (1:2) | 247–250 |
| 4 | —C(CH2)$_2$O— | —NH$_2$ | Cl | — | 217 |
| 5 | —O(CH2)$_3$O— | —NH$_2$ | Cl | HCl (1:2) | 191–198 |

In the "Salt" column, "—" denotes a compound in the baseform and "2HCl" denotes a dihydrochloride.

The compounds of the invention have formed the subject of tests which have demonstrated their advantage as substances possessing therapeutic activities.

Thus, their affinity for 5-HT$_3$ serotoninergic receptors was demonstrated by the displacement of the binding of a specific labelled ligand, [$^3$H]-(S)-zacopride.

The study is carried out in vitro on the 5-HT$_3$ receptors of the rat cortex, essentially as described by Barnes N. M. et al., J. Pharm. Pharmacol. (1988), 40, 548–551. Male Sprague-Dawley rats (OFA, Iffa Credo, Lyons, France), with a weight of 200 to 250 g, are humanely killed and the brain is removed. The cortex is subsequently dissected and homogenized using a Polytron™ mill (position 7, 20 s) in 20 volumes of Tris buffer (25 mM, ph=7.4 at 22° C.), the homogenate is centrifuged at 45,000 g for 10 min using a Sorvall™ centrifuge equipped with an SS34 rotor, and the pellet is resuspended in 10 volumes of Tris buffer and incubated at 37° C. for 10 min with stirring. The suspension is diluted to 20 volumes using Tris buffer and again centrifuged under the same conditions, and then the pellet is resuspended in 5 volumes of Tris buffer and divided into 5 ml aliquot fractions which are frozen at −80° C.

On the day of the experiment, the preparation is thawed at +4° C. and then diluted 1.2 times using Tris-NaCl incubation buffer (Tris 25 mM, NaCl 150 mM, pH=7.4 at 22° C.).

The membrane suspension (100 μl, 1 mg of proteins) is then incubated at 25° C. for 25 min in the presence of 0.5 nM of [$^3$H]-(S)-zacopride (specific activity 75–85 Ci/mmol, Amersham, Little Chalfont, Great Britain) in a final volume of 500 μl of Tris-NaCl buffer in the presence or in the absence of test compound.

The incubation is halted by filtration through Whatman GF/B filters pretreated with 0.1% polyethyleneimine. Each reaction tube is prediluted with 4 ml of Tris-NaCl buffer and then rinsed three times with 4.5 ml of of Tris-NaCl buffer.

The filters are cut up beforehand prior to drying in an oven (120° C., 5 min). The radioactivity retained on the filters is determined by liquid scintigraphy. The non-specific binding is determined in the presence of 10 μM of MDL 72222 (ligand described in the cited article). For each concentration of studied compound, the percentage of inhibition of the specific binding of [$^3$H]-(S)-zacopride and then the IC$_{50}$ concentration, the concentration of this compound which inhibits 50% of this specific binding, are determined. The IC$_{50}$ values of the compounds of the invention lie between 0.1 and 0.5 μm.

The compounds of the invention were also studied for their affinity with respect to 5-HT$_4$ receptors in the striatum of guinea pigs according to the method described by Grossman et al. in Br. J. Pharmacol., (1993) 109, 618–624. Guinea pigs (Hartley, Charles River, France) weighing 300 to 400 g are humanely killed, the brains are removed and the striata are excised and frozen at −80° C.

On the day of the experiment, the tissue is thawed at +4° C. in 33 volumes of HEPES-NaOH buffer (50 mM, pH=7.4 at 20° C.) and is homogenized using a Polytron® mill, the homogenate is centrifuged at 48,000 g for 10 min, the pellet is recovered, resuspended and recentrifigued under the same conditions and the final pellet is resuspended in HEPES-NaOH buffer, in the proportion of 30 mg of tissue per ml. 100 μl of this membrane suspension are incubated at 0° C. for 120 min in the presence of [$^3$H]GR113808 (ligand described in the cited article, specific activity 80–85 Ci/mmol) in a final volume of 1 ml of HEPES-NaOH buffer (50 mM, pH=7.4), in the presence or in the absence of test compound. Incubation is halted by filtration through a Whatman GF/B filter pretreated with 0.1% polyethyleneimine, each tube is rinsed with 4 ml of buffer at 0° C., filtration is again carried out and the radioactivity retained on the filter is measured by liquid scintigraphy.

The non-specific binding is determined in the presence of 30 μM serotonin. The specific binding represents 90% of the total radioactivity recovered on the filter. For each concentration of studied compound, the percentage of inhibition of the specific binding of [$^3$H]GR113808 and then the $IC_{50}$, the concentration of the test compound which inhibits 50% of the specific binding, are determined. The $IC_{50}$ values of the compounds of the invention lie between 0.015 and 5 μM.

The compounds of the invention were also studied as regards their agonist or antagonist effects with respect to 5-$HT_4$ receptors in the rat oesophagus, according to the method described by Baxter et al. in *Naunyn Schmied. Arch. Pharmacol.*, (1991) 343, 439. Male Sprague-Dawley rats weighing from 300 to 450 g are used. An approximately 1.5 cm fragment is quickly removed from the end part of the oesophagus, the muscular layer is removed and the internal muscular mucosal tunic is opened longitudinally, mounted in an isolated organ vessel containing a Krebs-Henseleit solution at 32° C. oxygenated by a carbogen stream (95% O2 and 5% $CO_2$) and connected to an isometric transducer under a basal tension of 0.5 g. A contraction of the tissue is induced by the addition of 05 μM of carbachol, there is a wait while the contraction becomes stabilized (15 min), and then the preparation is exposed to serotonin (1 μM) in order to quantify the maximum relaxation. The tissue is washed and, after a period of 20 min, 0.5 μM of carbachol is again added and the preparation is exposed to the study compound, in increasing additive concentrations from 0.1 to 1 μM. The compounds which induce a relaxation are characterized as 5-$HT_4$ agonists. For the compounds which do not induce relaxation, the preparation is exposed to serotonin in increasing additive concentrations, from 0.1 nM to a concentration inducing a maximum relaxation, and the relaxation curve due to serotonin, in the presence of the study compound, is then compared with a control curve prepared in the absence of the said compound. If its presence induces a shift of the curve towards the right, the study compound is characterized as a 5-$HT_4$ antagonist.

Finally, the compounds of the invention were studied as regards their antagonist effects with respect to 5-$HT_3$ receptors in the colon smooth muscle isolated from the guinea pig, according to the method described by Grossman et al. in *Br. J. Pharmacol.* (1989), 97, 451.

Serotonin (0.1–100 μM), after blocking the receptors of 5-$HT_1$ and 5-$HT_2$ types (0.1 μM methysergide) and desensitizing the 5-$HT_4$ receptors (10 μM 5-methoxytryptamine), causes a contraction, dependent on the concentration, of the smooth muscular part of the descending colon of the guinea pig, by stimulation of the 5-$HT_3$ receptors. The contractions are recorded by isometry.

The antagonist effect of a compound on the 5-$HT_3$ serotoninergic receptors is quantified by the measurement of the shift of a control concentration-effect curve of serotonin (non-additive increasing successive concentrations), at concentrations of the compound of between 1 nM and 0.1 μM, with an incubation of 30 min.

The results of the biological tests carried out on the compounds of the invention show that they are ligands for serotoninergic receptors of 5-$HT_3$ and/or 5-$HT_4$ types and that they act as 5-$HT_4$ agonists or antagonists and/or as 5-$HT_3$ antagonists.

The compounds can therefore be used for the treatment and prevention of disorders in which the 5-$HT_3$ and/or 5-$HT_4$ receptors are involved, whether at -he level of the central nervous system, of the gastrointestinal system, of the cardiovascular system or of the urinary system.

At the level of the central nervous system, these disorders and problems comprise in particular neurological and psychiatric disorders such as cognitive disorders, psychoses, compulsive and obsessional behaviours and states of depression and of anxiety. The cognitive disorders comprise, for example, memory and attention deficits, states of dementia (senile dementias of the Alzheimer's disease type or dementias related to age), cerebrovascular deficiencies or Parkinson's disease. The psychoses comprise, for example, paranoia, schizophrenia, mania and autism. The compulsive and obsessional behaviours comprise, for example, eating disorders of the loss of appetite or bulimia type. The states of depression and of anxiety comprise, for example, anxieties of anticipatory type (before a surgical operation, before dental treatment, and the like), the anxiety caused by dependence on or withdrawal from alcohol or drugs, man,-a, seasonal affective disorders, migraines or nausea.

At the level of the gastrointestinal system, these disorders and problems comprise in particular vomiting induced by an antitumour treatment, direct or indirect disorders of gastromotility of the oesophagus, of the stomach or of the intestines, or specific complaints, such as dyspepsia, ulcer, gastro-oesophagal reflux, flatulence, irritable bowel syndrome, disorders of intestinal secretion or diarrhoeas, for example those induced by cholera or by carcinoid syndrome.

At the level of the cardiovascular system, these disorders and problems comprise in particular pathologies related, directly or indirectly, to cardiac arrhythmias.

At the level of the urinary system, these disorders and problems comprise in particular incontinences of all kinds, as well as their causes or consequences, for example infections, stones or renal damage.

The compounds of the invention can be presented in all forms of compositions appropriate for enteral or parenteral administration, such as tablets, dragées, capsules, including hard gelatin capsules, suspensions or solutions to be swallowed or injected, such as syrups or phials, and the like, in combination with suitable excipients, and in doses which make possible a daily administration of 0.005 to 20 mg/kg.

We claim:

1. A compound in the form of a pure enantiomer or a mixture of enantiuomers, having the formula (I):

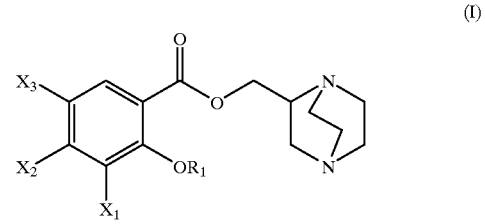

wherein
$R_1$ represents a methyl group, and
$X_1$ represents a hydrogen atom,
or
$OR_1$ and $X_1$ together form a group of formula —O(CH$_2$)$_2$—,
—O(CH$_2$)$_3$—, —O(CH$_2$)$_2$O— or —O(CH$_2$)$_3$O—,
$X_2$ represents a hydrogen atom or an amino group, and
$X_3$ represents a halogen atom,
in the form of the free base or of an addition salt with an acid.

2. A process for the preparation of compounds according to claim 1, comprising:
reacting piperazine and ethyl 2,3-dibromopropanoate to form ethyl 1,4-diazabicyclo[2.2.2]octane-2-carboxylate;

reducing ethyl 1,4-diazabicyclo[2.2.2]octane-2-carboxylate to form 1,4-diazabicyclo[2.2.2]octane-2-methanol;

reacting 1,4-diazabicyclo[2.2.2]octane-2-methanol with a benzoic acid derivative of formula (V):

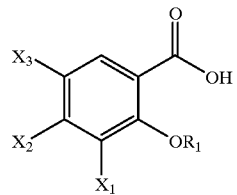

(V)

wherein $R_1$, $X_1$, $X_2$ and $X_3$ are as defined in claim 1; and optionally forming an addition salt with an acid.

3. A pharmaceutical composition, comprising a pharmaceutically effective amount of at least one compound according to claim 1, in combination with a pharmaceutically acceptable excipient.

4. A pharmaceutical composition according to claim 3, wherein the composition is in the form of a tablet, dragées, capsule, hard gelatin capsule, suspension or solution to be swallowed or injected, syrup, or phial.

5. A method of treating or preventing a serotonin-related disorder, comprising administering a pharmaceutically effective amount of at least one compound according to claim 1 to a patient in need thereof.

6. The method of claim 5, wherein said serotonin-related disorder is related to the 5-$HT_3$ receptors, 5-$HT_4$ receptors, or both.

7. The method of claim 5, wherein said disorder is involved at the level of the central nervous system, gastrointestinal system, cardiovascular system, or urinary system.

8. The method of claim 7, wherein said central nervous system disorder is selected from the group consisting of cognitive disorders, psychoses, compulsive behaviors, obsessional behaviors, depression, and anxiety.

9. The method of claim 8, wherein said cognitive disorder is selected from the group consisting of memory and attention deficits, states of dementia, Alzheimer's senile dementias, dementias related to age, cerebrovascular deficiencies, and Parkinson's disease.

10. The method of claim 8, wherein said psychoses are selected from the group consisting of paranoia, schizophrenia, mania, and autism.

11. The method of claim 8, wherein said compulsive behaviors or obsessional behaviors are the eating disorders loss of appetite or bulimia.

12. The method of claim 8, wherein said depression or anxiety disorders are selected from the group consisting of anticipatory anxiety, anxiety caused by dependence on or withdrawal from alcohol or drugs, mania, seasonal affective disorders, migraines, and nausea.

13. The method of claim 7, wherein said gastrointestinal system disorder is either vomiting induced by an antitumour treatment, or direct or indirect disorders of gastromotility of the oesophagus, stomach and/or intestines.

14. The method of claim 7, wherein said gastrointestinal system disorder is selected from the group consisting of dyspepsia, ulcer, gastro-oesophagal reflux, flatulence, irritable bowel syndrome, disorders of intestinal secretion, diarrhea, diarrhea induced by cholera, and diarrhea induced by carcinoid syndrome.

15. The method of claim 7, wherein said cardiovascular system disorder is a pathology related to cardiac arrhythmias.

16. The method of claim 7, wherein said urinary system disorder is incontinence.

17. The method of claim 7, wherein said urinary system disorder is a disorder related to the cause or consequence of incontinence, infections, stones, or renal damage.

* * * * *